US00PP21927P2

(12) United States Plant Patent
Bradford

(10) Patent No.: US PP21,927 P2
(45) Date of Patent: May 24, 2011

(54) NECTARINE TREE NAMED 'GIANT BRIGHT'

(50) Latin Name: *Prunus persica*
Varietal Denomination: Giant Bright

(76) Inventor: Lowell Glen Bradford, Le Grand, CA (US)

( * ) Notice: Subject to any disclaimer, the term of this patent is extended or adjusted under 35 U.S.C. 154(b) by 0 days.

(21) Appl. No.: 12/655,115

(22) Filed: Dec. 24, 2009

(51) Int. Cl.
*A01H 5/00* (2006.01)

(52) U.S. Cl. ..... Plt./190

(58) Field of Classification Search ..... Plt./190
See application file for complete search history.

(56) References Cited

U.S. PATENT DOCUMENTS

| | | | |
|---|---|---|---|
| PP7,049 | P | 10/1989 | Bradford |
| PP10,888 | P | 5/1999 | Bradford |
| PP11,477 | P | 8/2000 | Waldner et al. |

*Primary Examiner* — Susan B McCormick Ewoldt

(57) ABSTRACT

The present invention relates to a new and distinct variety of nectarine tree, *Prunus persica,* broadly characterized by a medium size, medium vigorous, hardy, self-fertile, medium productive and regular bearing tree. The variety blooms during the mid to late season and requires about 650 chilling hours. The fruit matures under the ecological conditions described in mid July, with first picking on Jul. 14, 2009. The fruit is uniformly large in size, acidic and sweet in flavor, globose in shape, clingstone in type, firm and melting in texture, mostly red in skin color, and nearly full yellow in flesh color.

1 Drawing Sheet

Botanical classification: *Prunus persica.*
Variety denomination: 'GIANT BRIGHT'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'GIANT BRIGHT'.

The present variety was hybridized by me in 2004 as a first generation cross using 'Western Pride' (U.S. Plant Pat. No. 10,888) nectarine as the selected seed parent and 'August Fire' (U.S. Plant Pat. No. 11,477) nectarine as the selected pollen parent. The fruit of this cross was gathered that summer, and the seeds were removed, cracked, stratified, germinated, and grown as seedlings on their own root in my greenhouse. Upon reaching dormancy the seedlings were transplanted as a group to a cultivated area of my experimental orchard located near Le Grand, Calif., in Merced County (San Joaquin Valley). During the fruit evaluation season of 2007 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Western Pride' nectarine, by producing nectarines that are firm, mostly red in skin color, very large in size, and acidic in flavor, but is distinguished therefrom by producing fruit that is clingstone instead of freestone and that matures about one week earlier.

The present variety is similar to its pollen parent, 'August Fire' nectarine, by producing nectarines that are nearly full red in skin color, clingstone in type, firm in texture, and acidic in flavor, but is distinguished therefrom by producing fruit that is larger in size and that matures about thirty days earlier.

The present variety is most similar to 'Summer Bright' (U.S. Plant Pat. No. 7,049) nectarine by producing nectarines that are nearly full red in skin color, clingstone in type, acidic in flavor, and that mature in mid July, but is distinguished therefrom by producing fruit that is substantially larger in size.

SUMMARY OF VARIETY

In summary, the present variety is characterized by a medium size, medium vigorous, hardy, self-fertile, medium productive and regular bearing tree. The variety blooms during the mid to late season and requires about 650 chilling hours. The fruit matures under the ecological conditions described in mid July, with first picking on Jul. 14, 2009. The fruit is uniformly large in size, acidic and sweet in flavor, globose in shape, clingstone in type, firm and melting in texture, mostly red in skin color, and nearly full yellow in flesh color.

DRAWING

The accompanying photograph consists of four whole fruits positioned to display the characteristics of the skin color and form, one sliced fruit to reveal the flesh and stone, three insets to reveal buds and a blossom, a typical tip shoot, and characteristic leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 19, 2009, on the original tree during its fifth growing season. The blossom and flower descriptions were made the previous blooming season. All major color code designations are by reference to the Inter-Society Color Council, National Bureau of Standards. Common color names are also used occasionally.

Parentage

Seed parent: 'Western Pride' nectarine (U.S. Plant Pat. No. 10,888).

Pollen parent: 'August Fire' nectarine (U.S. Plant Pat. No. 11,477).

Tree

Size: Medium, reaching and maintaining a height of 10' [3.05 m.] and a spread of 6' [1.83 m.] after five growing seasons utilizing typical dormant pruning.

Vigor: Medium vigor, responding typically to irrigation and fertilization. The variety grows about 3' [0.91 m.] of surplus top-growth during the spring and summer. The plant should be grown on a standard commercial rootstock for production purposes.

Growth: Upright and dense.

Form: Central leader.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Medium productive, thinning usually necessary.

Fertility: Self-fertile.

Bearing: Fairly consistent bearer with no alternate bearing yet observed.

Approximate chilling requirement: 650 hours.

Trunk:

- *Size.*—Medium, reaching a maximum diameter of 3⅛" [79 mm.] after the fifth growing season.
- *Texture.*—Shaggy.
- *Bark color.*—A Grayish brown [61. gy.Br] and Dark grayish reddish brown [47. d.gy.rBr] variegation.
- *Lenticels.*—Approximate Number Per Square Inch: 8. Color: Deep orange yellow [69. deep OY]. Average Size: 5/16" [8.0 mm.]. Shape: Eye-shaped, elongated.

Branches:

- *Size.*—Diameter of first side limb is 1¼" [32 mm.] measured 12" from the central leader.
- *Texture.*—Fairly smooth on first and second year wood, increasing roughness with age.
- *Color.*—1st Year Wood Topside: Grayish red [19. gy.R]. 1st Year Wood Underside: Brilliant yellow green [116. brill.YG]. 2nd Year Wood: Deep yellowish brown [75. deep yBr]. Older Wood: A Grayish brown [61. gy.Br] and Moderate brown [58. m.Br] variegation.
- *Lenticels.*—Number Per Square Inch: About 75 on second year wood. Color: Light yellowish brown [76. l.yBr]. Average size: 1/16" [1.6 mm.]. Shape: Eye-shaped, elongated.

Leaves:

- *Size.*—Medium. Average Length: 5½" [140 mm.]. Average Width: 1⅜" [35 mm.].
- *Arrangement.*—Alternate.
- *Thickness.*—Medium.
- *Form.*—Elliptical.
- *Apex.*—Acuminate.
- *Base.*—Acute to rounded, with an average base angle of 85 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Light yellow green [119. l.YG].
- *Petiole.*—Average Length: ⅜" [9.5 mm.]. Average Thickness: 1/16" [1.6 mm.]. Color: Moderate yellowish green [136. m.yG].
- *Stipules.*—Number: Usually 2 per leaf, up to 6 per growing tip. Average Length: ⅜" [9.5 mm.]. Color: Brilliant yellow green [116. brill.YG] becoming Moderate reddish brown [43. m.rBr] with maturity.
- *Glands.*—Number: Mostly 2 to 4 per leaf. Position: Mostly alternate, positioned near the intersection of the petiole and base of blade. Size: Large. Form: Mostly reniform. Color: Moderate yellow green [120. m.YG] becoming Dark yellowish brown [78. d.yBr] with age.
- *Leaf buds.*—Pointed, medium in size.

Flower buds:

- *Hardiness.*—Hardy, with respect to central California winters.
- *Diameter.*—Typically 5/16" [8.0 mm.] 1 week before bloom.
- *Length.*—Typically 7/16" [11.1 mm.] 1 week before bloom.
- *Form.*—Not appressed.
- *Surface.*—Pubescent.
- *Color.*—Deep pink [3. deep Pk].

Flowers: Perfect, complete, perigynous, usually a single pistil, about 24 stamens, five sepal and petal locations alternately positioned.

- *Type.*—Small.
- *Average flower diameter.*—⅞" [22.2 mm.].
- *Number of petals.*—Five, extra petal fragments are rare.
- *Petal shape.*—Oval.
- *Petal margin.*—Wavy.
- *Average petal diameter.*—⅜" [9.5 mm.].
- *Average petal length.*—½" [12.7 mm.].
- *Petal apex.*—Rounded.
- *Petal base.*—Acute.
- *Petal color.*—Deep pink [3. deep Pk] toward the margin and Pale purplish pink [252. p.pPk] toward the center on both sides.
- *Anther color.*—Moderate reddish orange [37. m.rO] over a Brilliant orange yellow [67. brill.OY] center, always protruding out of the bud before flower opening.
- *Stigma color.*—Light greenish yellow [101. l.gY].
- *Sepal color.*—Grayish purplish red [262. gy.pR].
- *Sepal length.*—¼" [6.4 mm.].
- *Sepal width.*—3/16" [4.8 mm.].
- *Average pistil length.*—⅝" [15.9 mm.], often protruding out of the bud before onset of bloom.

*Average stamen length.*—⅜" [9.5 mm.].
*Fragrance.*—Moderate.
*Blooming period.*—Medium to late, with 'Summer Bright' (U.S. Plant Pat. No. 7,049) nectarine.
*Onset of bloom.*—One percent on Mar. 3, 2009.
*Date of full bloom.*—Mar. 10, 2009.
*Duration of bloom.*—One to two weeks, dependent on ambient temperature.
*Number per cluster.*—1 to 3 with single flowers most common.

FRUIT

Maturity when described: Firm ripe, Jul. 19, 2009.
Date of first picking: Jul. 14, 2009.
Date of last picking: Jul. 24, 2009.
Size: Uniform, very large.
*Average diameter axially.*—3 1/16" [77.8 mm.].
*Average diameter across suture plane.*—3⅛" [79.4 mm.].
*Average diameter across cheek plane.*—3⅛" [79.4 mm.].
*Typical weight.*—9.3 ounces [264 grams].
Form: Uniform, globose, slightly asymmetrical.
*Longitudinal section form.*—Round to slightly oval.
*Axial view.*—Round.
Suture: A shallow groove inside the stem cavity, a shallow trough along the side, and a shallow groove toward the apex, extending just past the pistil point.
Ventral surface: Rounded, lipped throughout, slightly stronger toward the apex.
Lips: Usually unequal.
Cavity: Flaring, slightly elongated in the suture plane, suture showing on one side, Brilliant yellow [83. brill.Y] stem markings present.
*Depth.*—1 1/16" [17.5 mm.].
*Breadth.*—1½" [38.1 mm.].
Base: Rounded to truncate.
Apex: Rounded, but slightly cordate if viewed parallel to the suture.
Pistil point: Both apical and oblique, negligible in length, mostly depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Slightly astringent.
*Tendency to crack.*—None observed in dry season.
*Color.*—Dark red [16. d.R] smoothly blending into a Moderate reddish orange [37. m.rO] background with a little Moderate orange yellow [71. m.OY] freckling toward the apex.
Flesh:
*Color.*—Brilliant yellow [83. brill.Y] with minimal Moderate red [15. m.R] streaking next to stone.
*Surface of pit cavity.*—Covered with Moderate red [15. m.R] broken fibers when twisted from stone.
*Amygdalin.*—Moderate.
*Juice.*—Moderate, rich.
*Texture.*—Firm, crisp.
*Fibers.*—Abundant, tough.
*Ripens.*—Slightly earlier at the apex.
*Flavor.*—Acidic and sweet, typically 16 brix.
*Aroma.*—Slight.
*Eating quality.*—Excellent.

STONE

Type: Clingstone.
Form: Oval.
Hilum: Narrow, oblong.
Base: Straight to slightly rounded.
Apex: Obtuse with an average angle of 105 degrees.
Sides: Equal.
Surface: Irregularly furrowed and ridged toward the apex, pitted toward the base.
Ridges: Jagged.
External color: Brownish orange [54. brO].
Pit wall color when cracked: Light yellowish brown [76. l.yBr].
Cavity surface color: A Dark yellowish brown [78. d.yBr] and Light yellowish brown [76. l.yBr] two-tone.
Average pit wall thickness: ¼" [6.4 mm.]
Average width: 1" [25.4 mm.].
Average length: 1½" [38.1 mm.].
Average breadth: ⅞" [22.2 mm.].
Tendency to split: Slight.
Kernel:
*Form.*—Oval.
*Skin color.*—Light yellow [86. l.Y] when first removed.
*Pellicle color.*—Grayish yellowish brown [80. gy.yBr].
*Vein color.*—Dark orange yellow [72. d.OY].
*Taste.*—Sweet.
*Viable.*—Yes.
*Average width.*—½" [12.7 mm.].
*Average length.*—⅝" [15.9 mm.].
*Amygdalin.*—Scant.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to 'Summer Bright' (U.S. Plant Pat. No. 7,049) nectarine by producing nectarines that are nearly full red in skin color, yellow in flesh color, clingstone in type, acidic in flavor, and that mature in mid July, but is distinguished therefrom by producing fruit that is substantially larger in size.

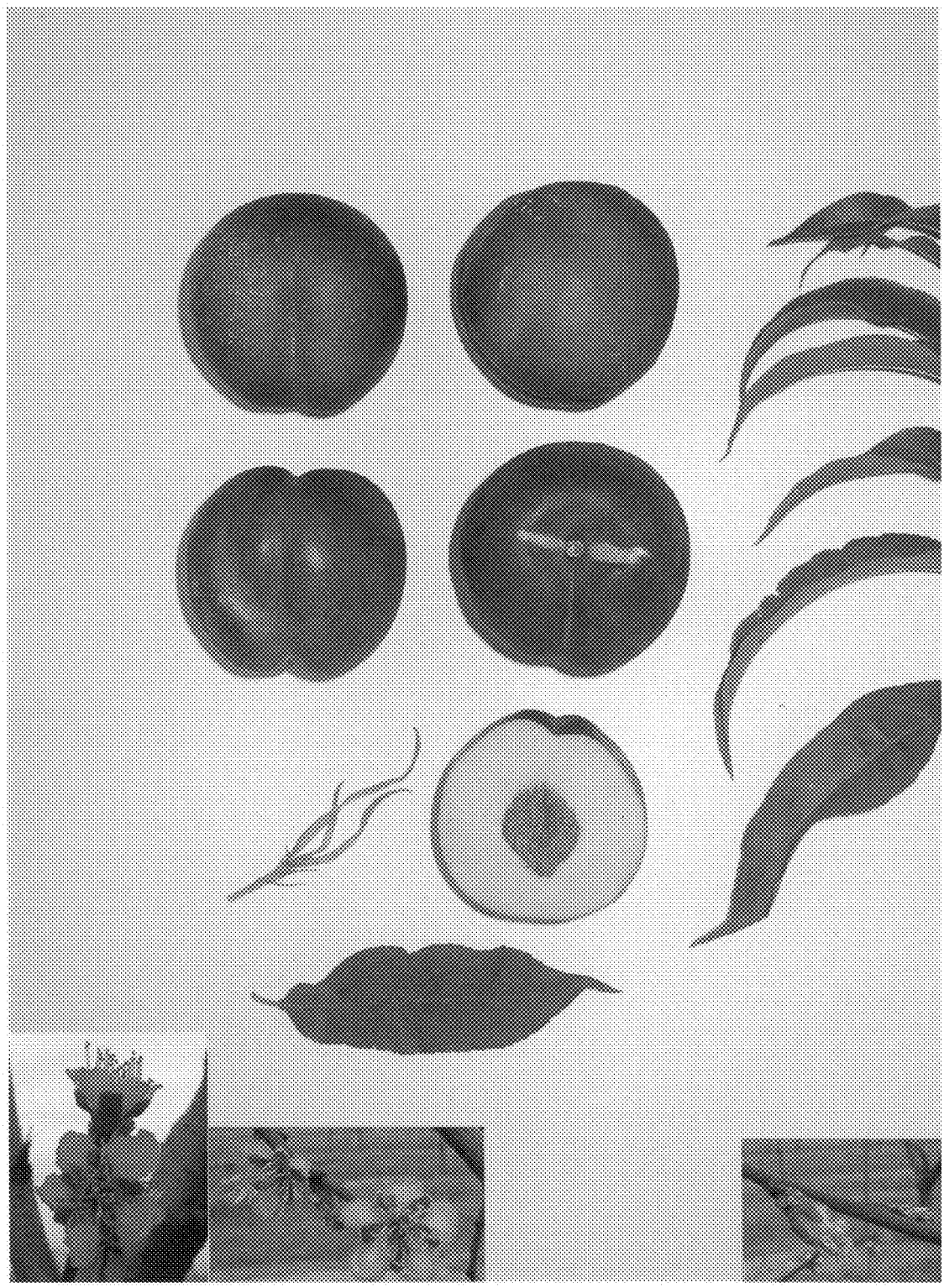

* * * * *